United States Patent
Liu

(10) Patent No.: US 9,504,630 B2
(45) Date of Patent: Nov. 29, 2016

(54) NASOGASTRIC TUBE

(71) Applicant: Changhua Christian Hospital, Changhua (TW)

(72) Inventor: Sen-Yung Liu, Huatan Township (TW)

(73) Assignee: Changhua Christian Hospital, Changhua (TW)

( * ) Notice: Subject to any disclaimer, the term of this patent is extended or adjusted under 35 U.S.C. 154(b) by 82 days.

(21) Appl. No.: 13/924,854

(22) Filed: Jun. 24, 2013

(65) Prior Publication Data

US 2014/0378907 A1    Dec. 25, 2014

(51) Int. Cl.
*A61J 15/00*    (2006.01)
*A61M 39/10*   (2006.01)

(52) U.S. Cl.
CPC ......... *A61J 15/0026* (2013.01); *A61J 15/0057* (2013.01); *A61M 39/10* (2013.01); *A61J 15/0003* (2013.01); *A61M 2039/1016* (2013.01); *A61M 2039/1027* (2013.01); *A61M 2039/1033* (2013.01); *A61M 2209/088* (2013.01)

(58) Field of Classification Search
CPC ................ A61M 2039/1027; A61M 39/1011; A61M 16/0666; A61M 16/0683; A61M 16/06; A61M 25/02; A61M 2210/0618; A61M 39/10; A61M 2039/1016; A61M 2039/1033; A61M 2209/088; A61J 15/0003; A61J 15/0011; A61J 15/0092; A61J 15/011; A61J 15/16; A61J 15/0026
USPC ....... 604/533–39, 178, 905, 265; 128/207.11
See application file for complete search history.

(56) References Cited

U.S. PATENT DOCUMENTS

| 3,568,678 | A | * | 3/1971 | Pourquier et al. ............ 604/174 |
| 4,660,555 | A | * | 4/1987 | Payton ...................... 128/207.18 |
| 4,969,879 | A | * | 11/1990 | Lichte ................... A61M 39/10 285/319 |
| 2005/0011524 | A1 | * | 1/2005 | Thomlinson et al. ... 128/207.18 |
| 2008/0190436 | A1 | * | 8/2008 | Jaffe et al. ............... 128/207.18 |
| 2009/0101154 | A1 | * | 4/2009 | Mutti et al. .............. 128/207.18 |
| 2012/0048277 | A1 | * | 3/2012 | Waldron et al. ......... 128/207.14 |

* cited by examiner

Primary Examiner — Bradley Osinski
(74) Attorney, Agent, or Firm — Rosenberg, Klein & Lee

(57) ABSTRACT

A nasogastric tube includes a connector. The connector has a first connection end, a second connection end and a flow channel formed through the connector. The first connection end is connected to a first tube, and the second connection end has a positioning sleeve formed thereon. The positioning sleeve has a connection part extended from the flow channel and jointing with an assembling part of the second tube. The first tube of nasogastric tube of the present invention can be inserted to a stomach from a nasal cavity, and then the connector is placed in the nasal cavity, and the positioning sleeve is fixed in the nostril. The second tube can be detached from the connector when not being used.

7 Claims, 5 Drawing Sheets

NASOGASTRIC TUBE

FIELD OF THE INVENTION

The present invention relates to a nasogastric tube, especially to a nasogastric tube having two parts that can be assembled and detached easily.

DESCRIPTION OF RELATED ART

As shown in FIG. 5, a conventional nasogastric tube has a first tube 50 introducible into a stomach. One end of the first tube 50 has a setting part 51 used for setting in a nasal cavity. The setting part 51 has a binding end 52 mounted thereon that can be connected to a second tube 53 upon feeding patients, and liquid food or nutrient solution is fed into the stomach of a patient via the second tube 53.

However, as shown in the figure, the structure of the conventional nasogastric tube is using the way of insertion, and wave-shaped buckling parts 54A and 54B, are formed to prevent from the whole structure from coming off. Nevertheless, the disadvantage of the buckling parts is the tightness of combination, which might inadvertently disengage each from the other if the combination is too loose, and if too tight the second tube 53 will be difficult to detach when not being used such that a part of the nasogastric tube inserted within a human body could be inadvertently dragged out by over-pulling. Additionally, the nasogastric tube is a kind of invasive medical instrument, so it is hard to place the nasogastric tube in a body. If pulling it out without care, there would be problems of subsequent repeated insertion and sanitation.

SUMMARY OF THE INVENTION

The main objective of the present invention is to provide a nasogastric tube having a combined structure which is easy to assemble and detach, and can improve the convenience and safety of use.

The second connection end 32 of the connector 3 has multiple through holes formed through the axial surface 321 and around the assembling part 21 such that the multiple through holes can be disposed in the human nasal cavity 4 and communicated to an external connection tube for breathing.

To achieve the main objective, the present invention provides a nasogastric tube comprising:
 a first tube;
 a second tube, having two ends and an assembling part formed on one end of the second tube;
 a connector, having a first connection end connected to the first tube, a second connection end, a flow channel formed through the connector and located between the first connection end and the second connection end, a positioning sleeve formed on the second connection end and extended to form a connection part from the flow channel that the connection part is connected to the assembling part of the second tube;
 wherein the connector is provided for placement in a human nasal cavity and fixed into a nostril using the positioning sleeve, and a part of the positioning sleeve is protruding out of the nostril.

Furthermore, the connection part of the connector has an internal thread formed thereon, and the assembling part of the second tube has an external thread formed thereon for joint with the internal thread.

Furthermore, the connection part of the connector has a ring, the assembling part of the second tube also has a ring used for being connected to the ring of the connection part.

DETAILED DESCRIPTION OF THE PREFERRED EMBODIMENTS

Figure 1:
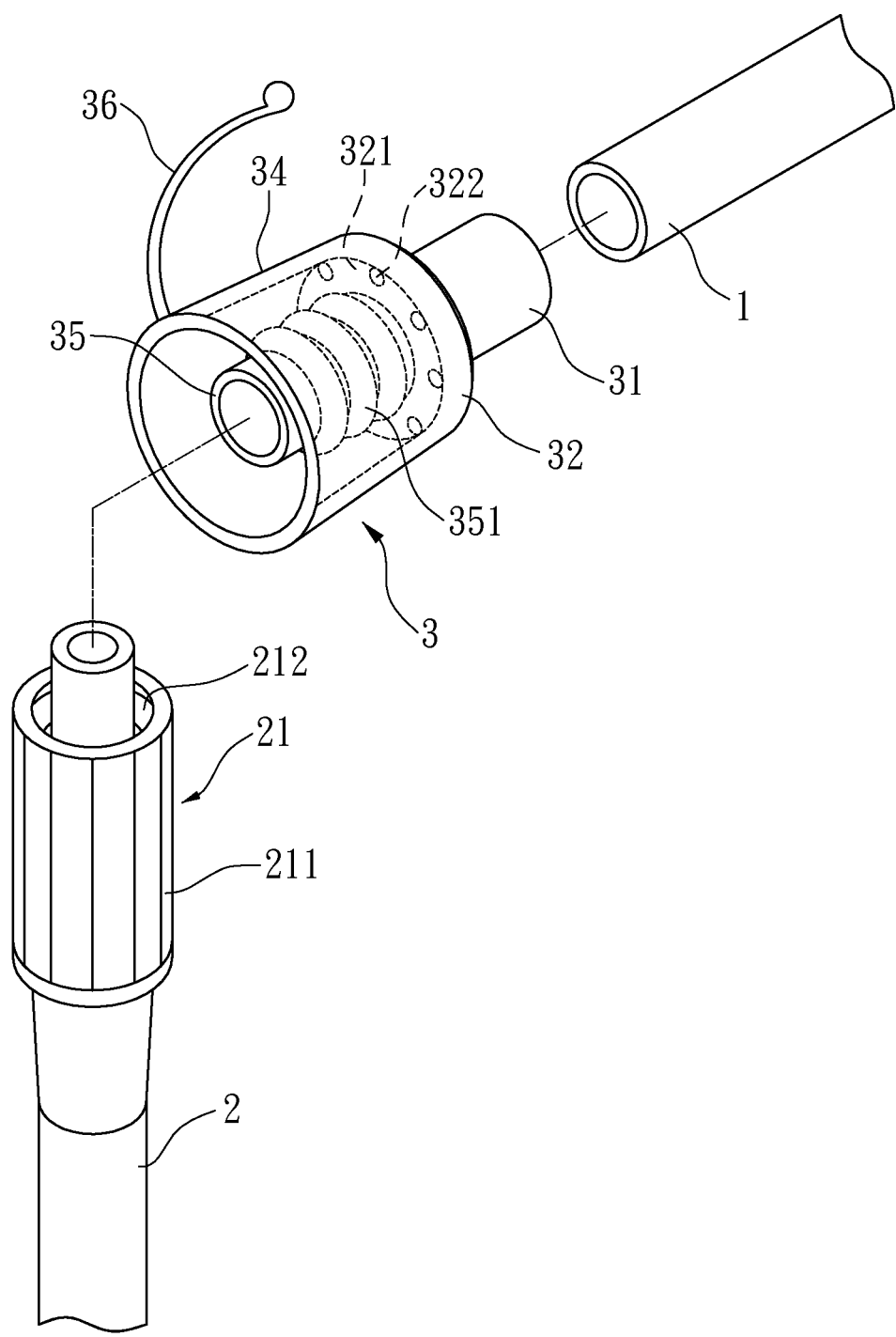
FIG. 1 is an exploded perspective view of the first embodiment of a nasogastric tube in accordance with the present invention.
Figure 2:
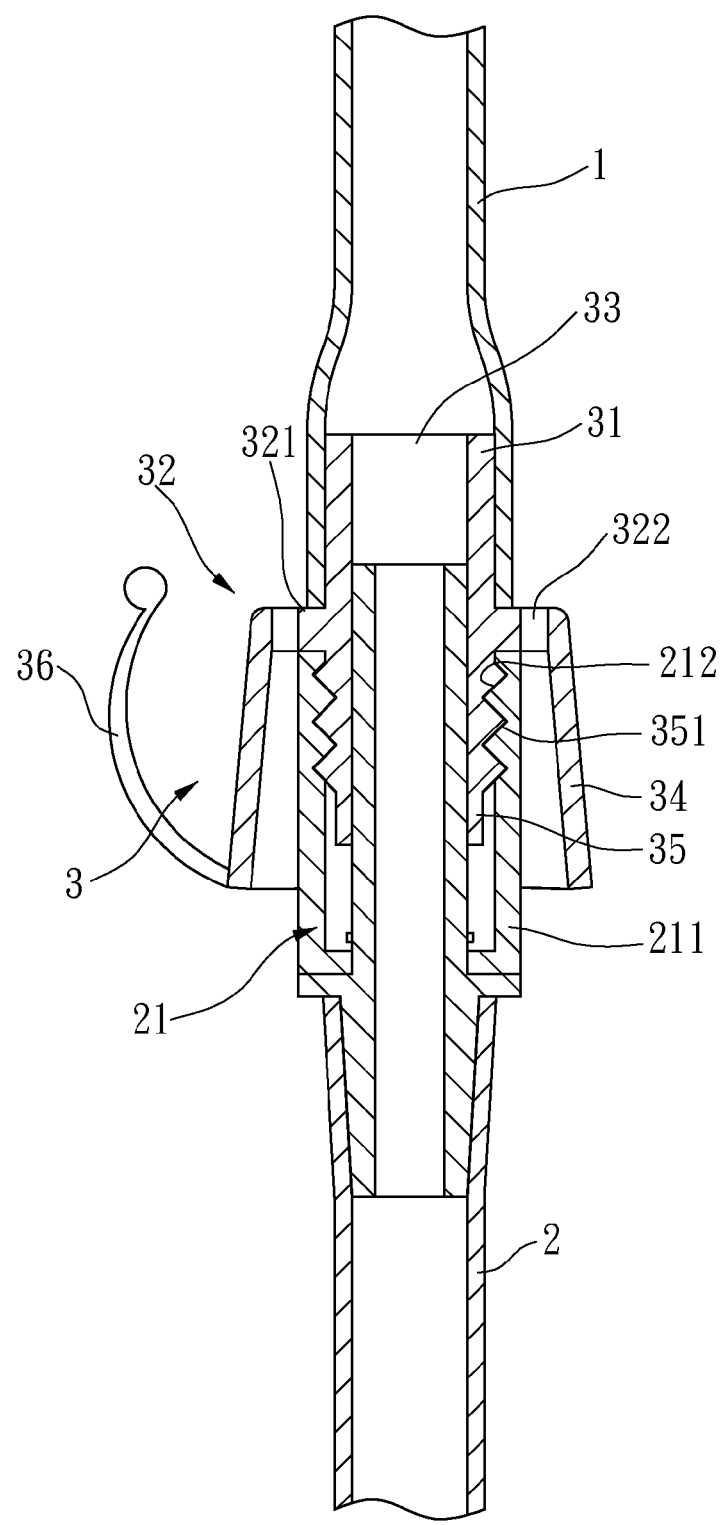
FIG. 2 is a sectional view of the first embodiment of a nasogastric tube in accordance with the present invention.

With reference to FIG. 1 and FIG. 2, a first embodiment of a nasogastric tube in accordance with the present invention comprises a first tube 1, a second tube 2 and a connector 3.

The connector 3 has a first connection end 31, a second connection end 32, and a flow channel 33 formed through the connector 3 and located between the first connection end 31 and the second connection end 32. In a preferred embodiment, the first connection end 31 of the connector 3 is ultrasonicly welded or glued securely to the first tube 1.

The second connection end 32 has an axial surface 321 formed around the second connection end 32, and a positioning sleeve 34 formed on the axial surface 321 far from the second connection end 32. The positioning sleeve 34 is provided for placement in a human nasal cavity and fixed into a nostril using the positioning sleeve 34. In a preferred embodiment, the positioning sleeve 34 is made of thermoplastic material compatible to a human body and formed into a device having a smooth surface, and is divergently cone-shaped from the second connection end 32. Furthermore, the external diameter of the positioning sleeve 34 near the second connection end 32 is smaller than that of a nostril, and the external diameter of the positioning sleeve 34 far from the second connection end 32 is bigger than that of a nostril.

A connection part 35 is tube-shaped and extended from the flow channel 33. The connection part 35 can be connected to the second tube 2. An assembling part 21 is formed on one end of the second tube 2. The assembling part 21 is connected to the connection part 35 of the connector 3.

In a preferred embodiment, the connection part 35 of the connector 3 has an internal thread 351 formed thereon. The second tube 2 has a sleeve 211 formed on the second tube 2, and the assembling part 21 of the second tube 2 has an external thread 212 formed thereon for jointing with the internal thread 351.

The connector 3 and the second tube 2 are jointing by the internal thread 351 and the external thread 212 and formed an integral nasogastric tube.

Figure 3:
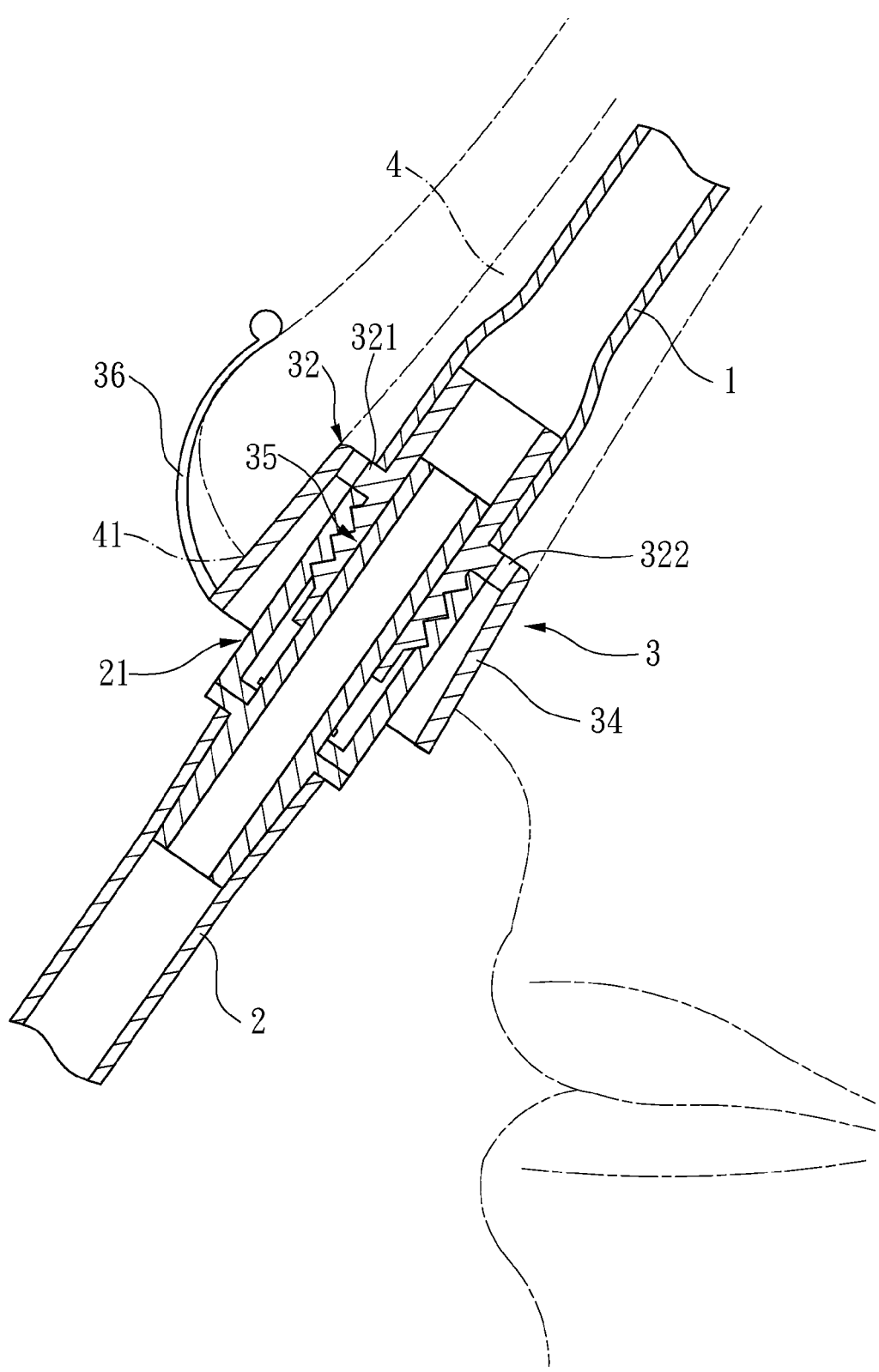
FIG. 3 is a sectional view of the first embodiment of a nasogastric tube in accordance with the present invention, showing the nasogastric tube being used.

With reference to FIG. 3, when the first embodiment of the nasogastric tube as described is used, the first tube 1 of the nasogastric tube is inserted to a human stomach (not shown) from the human nasal cavity 4. The connector 3 is placed in the human nasal cavity 4 and the positioning sleeve 34 is fixed into a nostril 41.

The second connection end 32 of the connector 3 has multiple through holes formed through the axial surface 321 and around the assembling part 21 such that the multiple through holes can be disposed in the human nasal cavity 4 and communicated to an external connection tube for breathing.

Furthermore, the positioning sleeve 34 is divergently cone-shaped and the external diameter of one end of the positioning sleeve 34 is smaller than that of a nostril, and the external diameter of the other end of the positioning sleeve 34 is bigger than that of a nostril, such that the positioning sleeve is fixed into the nostril and a part of the positioning sleeve 34 is protruding out of the nostril.

The depth of the positioning sleeve 34 inserted in the nostril 41 of a user depends on the size of the nostril 41. The depth can be adjusted to avoid discomfort to the user when inserted into the nostril 41. The positioning sleeve 34 has a hook 36 formed thereon. After placing the positioning sleeve 34 in the nostril 41, the hook 36 grips the alae of a user's nose for better positioning.

Furthermore, the external thread 212 of the second tube 2 is coupled with the internal thread 351 of the connector 3 when the nasogastric tube of the present invention is used for feeding. Because the external thread 212 and the internal thread 351 are engaged by rotation, the second tube 2 and the connector 3 cannot easily fall out in the axial direction.

In another aspect, when the user finishes using the nasogastric tube and wants to detach the second tube 2 from the connector 3, the user will rotate the second tube 2 relative to the connector 3 so as to detach the second tube 2 from the connector 3. This reduces the risk of the user inadvertently pulling out the nasogastric tube previously inserted into a human body, thereby, enhancing the safety of use.

Figure 4:
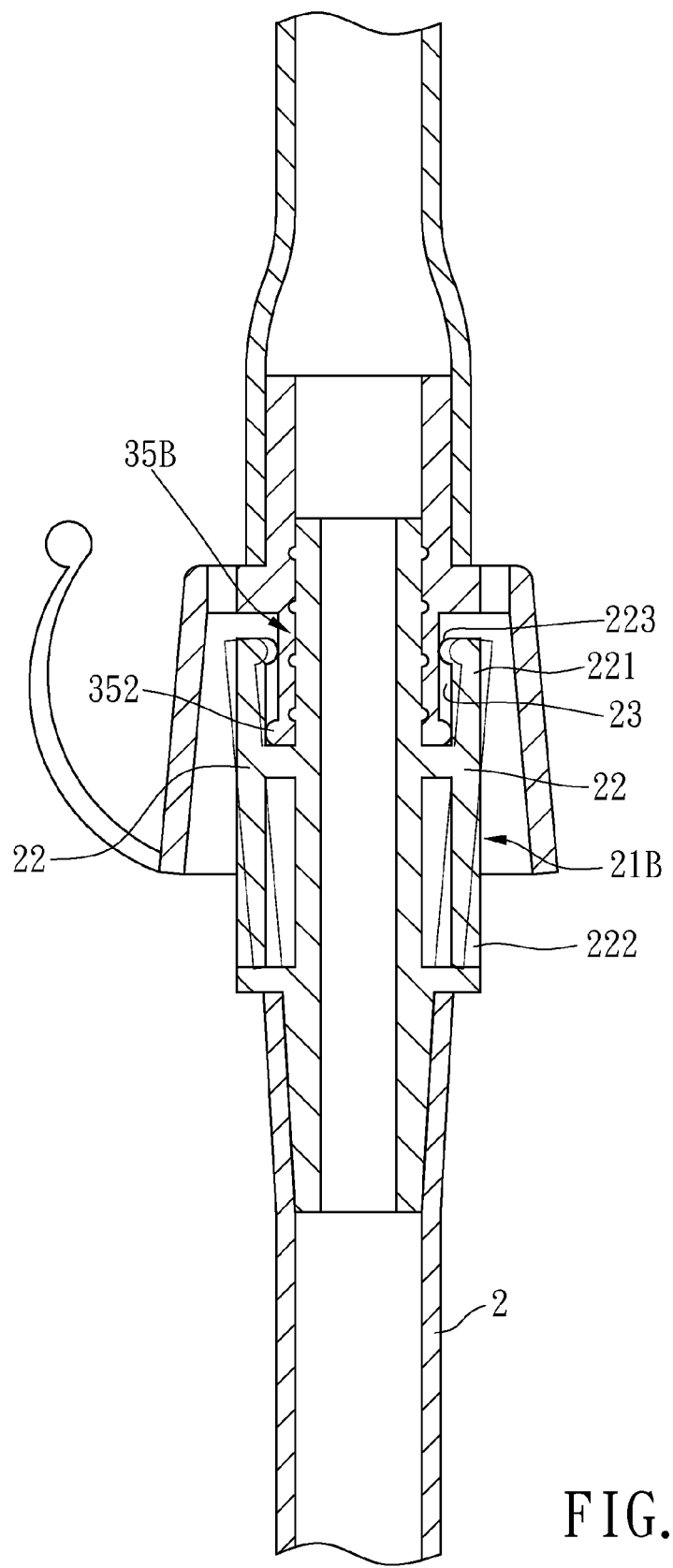
FIG. 4 is a sectional view of the second embodiment of a nasogastric tube in accordance with the present invention.
Figure 5:
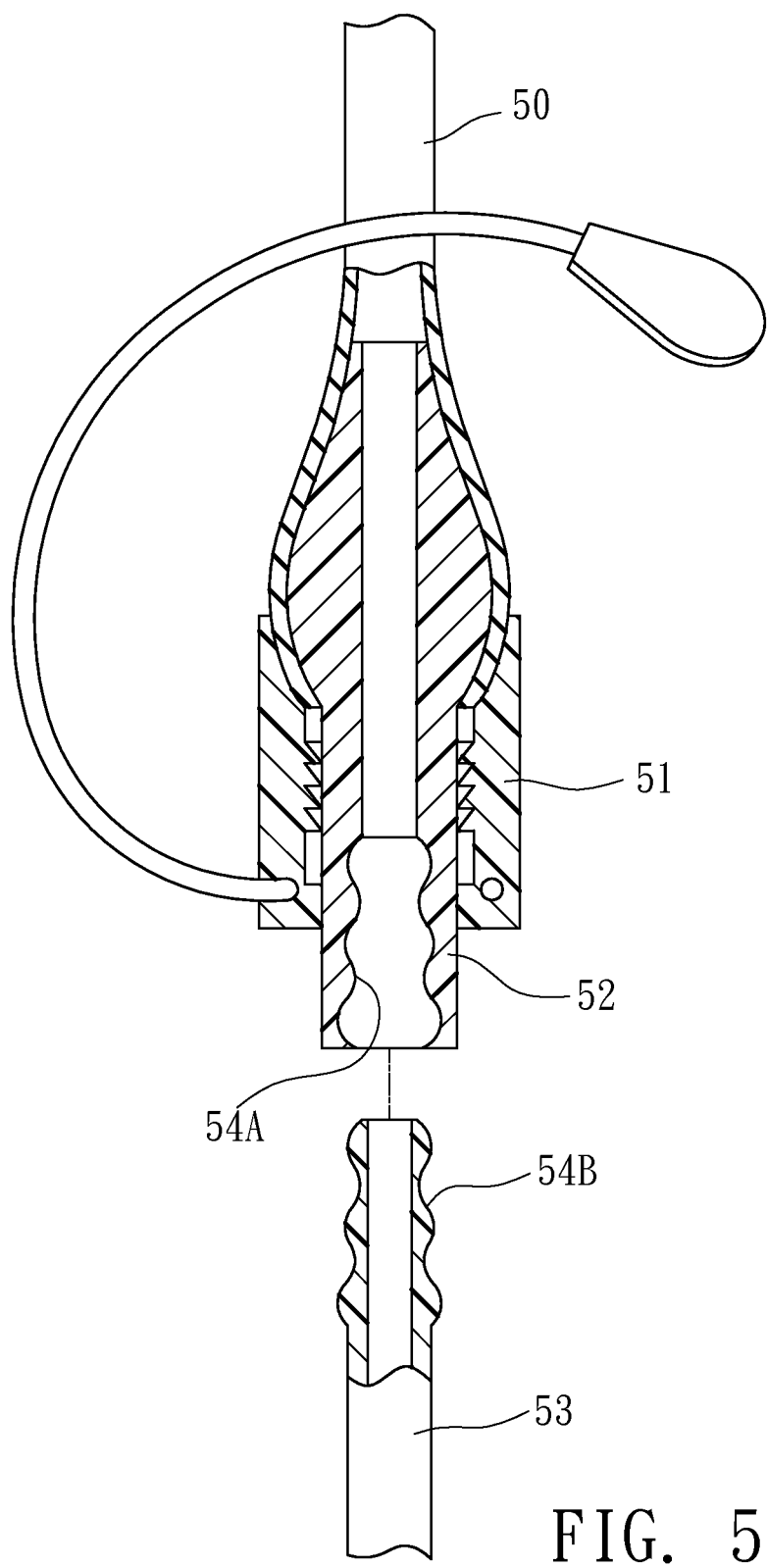
FIG. 5 is a sectional view of a conventional nasogastric tube.

With reference to FIG. 4 for a side view of a second embodiment of a nasogastric tube in accordance with the present invention, the difference of the second embodiment and the first embodiment is the structure of the connector 3 and the second tube 2. In this embodiment, the connection part 35B of the connector 3 is tube-shaped and has a flange 352 formed outward from the end of the connection part 35B to two sides of the connection part 35B. The assembling part 21B of the second tube 2 has a pair of locking units 22. The pair of locking units 22 is located at the two sides of the assembling part 21B respectively and formed a gap 23 therein.

The middle part of the locking unit 22 is connected to the assembling part 21B. The locking unit 22 is made of flexible material. The locking unit 22 has a first end 221 and a second end 222. The first end 221 and the second end 222 can be pivoted on the position of connection of the locking unit 22 and the assembling part 21B. The locking unit 22 has a stopper 223 formed inward on the first end 221 of the locking unit 22. The stopper 223 of the locking unit 22 is used for blocking the flange 352 inserted in the gap 23 between the assembling part 21B of the second tube 2 and locking unit 22 to be withdrawn reversibly when the connector 3 is connected to the second tube 2, thereby forming stable construction. The second end 222 of the locking unit 22 is pressed to make the stopper 223 of the first end 221 pivoted backward and open when detaching the second tube 2. Accordingly, the present invention in this embodiment also has the convenience of stable combination and high safety of detaching the second tube 2.

What is claimed is:

1. A nasogastric tube, comprising:
a first tube;
a second tube, having two ends and an assembling part formed on one end of the second tube;
a connector disposed between the first tube and the second tube to define a flow channel therebetween, a first connection end of the connector being connected to the first tube, a second connection end of the connector being connected to the second tube, a positioning sleeve formed on the second connection end and extending to form a connection part from the flow channel that connects and fluidly communicates with the assembling part of the second tube, the positioning sleeve and the connection part being laterally offset one from the other by a gap formed therebetween;
wherein a displaceable locking unit disposed on the assembling part is displaced to engage or disengage a flange portion of the connection part, the displaceable locking unit having opposing first and second ends for releasable engagement with the connection part, the positioning sleeve being disposed to encompass an upper portion of the displaceable locking unit, the connection part having the flange portion at a lower section of the connection part, said first end of said displaceable locking unit being pivotably displaceable within the gap upon compressive force applied to the second end of the locking unit for release of the first end from interference with the flange portion, the connector is adapted for placement in a human nasal cavity and adapted for placement into a nostril using the positioning sleeve, and a part of the positioning sleeve is adapted to protrude out of the nostril.

2. The nasogastric tube as claimed in claim 1, wherein the positioning sleeve has a hook formed thereon, and provided for griping an alae of a human nose.

3. The nasogastric tube as claimed in claim 1, wherein the positioning sleeve is divergently cone-shaped from the second connection end of the connector, wherein the external diameter of the positioning sleeve near the second connection end is smaller than that of a nostril, while the external diameter of the positioning sleeve far from the second connection end is bigger than that of a nostril.

4. The nasogastric tube as claimed in claim 1, wherein the second connection end of the connector has multiple through holes formed around the assembling part.

5. The nasogastric tube as claimed in claim 1, wherein the positioning sleeve of the connection part is made of thermoplastic material compatible to a human body and formed into a device having a smooth surface.

6. The nasogastric tube as claimed in claim 1, wherein the first connection end of the connector is ultrasonically welded to the first tube.

7. The nasogastric as claimed in claim 1, wherein the first connection end of the connector is glued securely to the first tube.

* * * * *